(12) United States Patent
Bringedal (10) Patent No.: US 12,049,329 B2
(45) Date of Patent: Jul. 30, 2024

(54) FUELING SYSTEM FOR AN AIRCRAFT, A METHOD FOR OPERATING THE FUELING SYSTEM AND USE OF SUCH FUELING SYSTEM

(71) Applicant: Imenco AS, Haugesund (NO)

(72) Inventor: Rune Bringedal, Haugesund (NO)

(73) Assignee: Imenco AS, Haugesund (NO)

( * ) Notice: Subject to any disclaimer, the term of this patent is extended or adjusted under 35 U.S.C. 154(b) by 188 days.

(21) Appl. No.: 17/776,372

(22) PCT Filed: Nov. 17, 2020

(86) PCT No.: PCT/NO2020/050282
§ 371 (c)(1),
(2) Date: May 12, 2022

(87) PCT Pub. No.: WO2021/101389
PCT Pub. Date: May 27, 2021

(65) Prior Publication Data
US 2022/0396374 A1 Dec. 15, 2022

(30) Foreign Application Priority Data
Nov. 21, 2019 (NO) .................................. 20191389

(51) Int. Cl.
*B64F 1/28* (2006.01)
*B67D 7/04* (2010.01)
(Continued)

(52) U.S. Cl.
CPC .................. *B64F 1/28* (2013.01); *B67D 7/04* (2013.01); *G01N 1/10* (2013.01); *G01N 33/22* (2013.01); *G01N 33/2847* (2013.01)

(58) Field of Classification Search
CPC .... B64F 1/28; B67D 7/04; G01N 1/10; G01N 33/22; G01N 33/2847
See application file for complete search history.

(56) References Cited

U.S. PATENT DOCUMENTS 4,932,609 A * 6/1990 Secchiaroli ............. B64C 17/10
244/135 C
5,200,064 A * 4/1993 Russ ................... G01N 33/2829
356/70

(Continued)

FOREIGN PATENT DOCUMENTS

| EP | 3050808 | 8/2016 |
|---|---|---|
| WO | 96/22222 | 7/1996 |
| WO | 2019/137919 | 7/2019 |

OTHER PUBLICATIONS

Supplementary European Search Report for EP 20890273, dated Oct. 24, 2023.

(Continued)

*Primary Examiner* — Nicolas A Arnett
(74) *Attorney, Agent, or Firm* — Andrus Intellectual Property Law, LLP (57) ABSTRACT

A fueling system is for an aircraft having a tank with a compartment configured to be filled with fuel. A discharge conduit extends from the compartment to an outside of the tank. A sampling arrangement has a sample container and a sample conduit extending from the compartment to the sample container. The fueling system further has a gas propellant arrangement comprising a pressurized gas source. The gas propellant arrangement is configured to provide pressurized gas to the compartment and to the sample container.

23 Claims, 4 Drawing Sheets (51) Int. Cl.
*G01N 1/10* (2006.01)
*G01N 33/22* (2006.01)
*G01N 33/28* (2006.01)

(56) References Cited

U.S. PATENT DOCUMENTS

| | | | | |
|---|---|---|---|---|
| 5,582,366 | A * | 12/1996 | Hamant | B64G 5/00 244/135 R |
| 7,377,151 | B1 * | 5/2008 | Magee | G01N 33/2847 73/61.61 |
| 9,045,238 | B2 * | 6/2015 | Lohmann | B64F 1/28 |
| 10,364,139 | B2 * | 7/2019 | Hutchinson | B67D 7/766 |
| 2003/0094543 | A1 * | 5/2003 | Matos | A62C 3/06 244/135 R |
| 2012/0210769 | A1 * | 8/2012 | Roper | G01N 33/2847 73/23.31 |
| 2013/0032672 | A1 * | 2/2013 | Fenton | B64F 1/28 244/135 R |
| 2016/0362195 | A1 * | 12/2016 | Wilkinson | B67D 7/04 |

OTHER PUBLICATIONS

"Standards for Offshore Helicopter Landing Areas", CAP 437. Published by the Civil Aviation Authority in Dec. 2016.
Norwegian Search Report for No. 20191389, dated Jan. 30, 2020.
International Search Report and the Written Opinion for PCT/NO2020/050282, dated Feb. 3, 2021.

* cited by examiner

Fig. 3

FUELING SYSTEM FOR AN AIRCRAFT, A METHOD FOR OPERATING THE FUELING SYSTEM AND USE OF SUCH FUELING SYSTEM

CROSS-REFERENCE TO RELATED APPLICATIONS

This application is the U.S. national stage application of International Application PCT/NO2020/050282, filed Nov. 17, 2020, which international application was published on May 27, 2021, as International Publication WO 2021/101389 in the English language. The International Application claims priority of Norwegian Patent Application No. 20191389, filed Nov. 21, 2019. The international application and Norwegian application are both incorporated herein by reference, in entirety.

INTRODUCTION

The present invention relates to a fueling system for an aircraft. The system comprises a tank comprising a compartment configured to be filled with fuel, a discharge conduit extending from the compartment to an outside of the tank, and a sampling arrangement comprising a sample container and a sample conduit extending from the compartment to the sample container.

The present invention further relates to a method for operating the fueling system of the invention and use of such fueling system.

PRIOR ART

Fueling systems for aircrafts are used for storing large amounts of fuel for refueling the aircrafts. The fueling systems may be remotely arranged and store fuel for a long period of time before being filled into an aircraft. The fueling systems are for example arranged at offshore windfarm parks for refueling helicopters used for transporting personnel in connection to maintenance work.

Publication US2016362195 A1 discloses a fuel delivery system and method for transferring fuel to an aircraft using a compressible gas, and in which the fuel tank includes a water sump with a drain valve to remove liquid water from the volume of fuel.

Publication US2013032672 A1 discloses a fueling system for an aircraft, wherein a pressure vessel includes a gas reservoir wherein the gas in the reservoir is pressurized to force fuel under a head of gaseous pressure out of a bladder.

Publication WO9622222 A1 discloses a satellite fueling system and method in which fuel is driven by means of helium into the satellite fuel tank.

Prior art fueling systems typically comprise several fuel tanks provided with numerous connections and valves at a bottom part or lower portions of the tank. Such connections and valves at a bottom or at lower portions of the tank represents a risk of leakage of a hazardous fluid exposed to personnel and atmosphere. Spilled fuel for a helicopter for example, may represent a risk of fire. To collect at least a portion of a fuel that may leak from one or more tanks, the tanks are arranged in a collection tray arranged at the installation, such as an offshore installation.

It is important to prevent water from entering the compartment of the tank for secure safe operation of the engines of the aircrafts. Water may typically seep into the tank at connecting penetrating a wall of the tank. Accordingly, it must be assured that sealing at the connections and valves are functional in preventing water from passing into the compartment of the tank. To assure the quality of the fuel, samples of the fuel from the compartment of the tank are also taken out prior and subsequently to refuelling the aircrafts.

Moreover, according to publication "CAP 437—Standards for offshore helicopter landing areas" tanks for fueling system should be provided with a free vent for equalising pressure fluctuation caused by changing ambient temperatures and caused during filling/bleeding of the tank. However, moisture in air that is entering through such a free vent may condensate within the compartment of the tank and entering the fuel. Due to difference in gravity of water and fuel, the water will concentrate in a bottom portion of the compartment of the tank. Water in fuel is one of the most critical factors for safe operation of an aircraft. There is therefore a requirement that samples from the fuel in the tanks are collected on a daily basis. CAP 437 requires a test sample of minimum 3 litres from each tank. After having been analysed, the test sample should be discarded. The test samples are collected manually via a valve in a bottom portion of the tank. A test sample collected manually by an operator results in that the operator may be exposed to the fuel. Furthermore, there is a risk of leakage from the tank in case of a failing valve at an opening of the drainage for collecting the test sample.

Prior art fueling systems are provided with pumps for discharging the fuel from the tank when refueling the aircraft. Usually, positive displacement pumps or centrifugal pumps are used. During sampling from the tank, it is required that the system is pressurized, which means that the pumps are running against closed outlet and with no flow conditions, which generates heat into the fuel. The fuel generally has a low flashpoint, such as 38 degree C., and the heat from the pumps therefore represents a potential risk to the fueling system. Furthermore, the pumps are associated with noise and vibration. The couplings and motors of the pumps also need maintenance for reliable operation of the fueling system.

The above-mentioned sampling operation is usually done manually and exposes the operator to the fuel. The samples are withdrawn from open pipe ends where there is a risk that the samples are contaminated with water from rain or the humidity in the air. Furthermore, the fuel samples can normally not be used for refuelling the aircraft and the fuel from the samples is therefore discarded.

SUMMARY OF THE INVENTION

The invention has for its object to remedy or to reduce at least one of the drawbacks of the prior art, or at least provide a useful alternative to prior art. In particular, an object of the invention is to provide an improved fueling system that reduces the risk of contamination of water in the fuel in the tank and a sample taken from the tank. A further object of the invention is to provide an improved fueling system that reduces risk of exposure of an operator to the fuel and which enables a sample of the fuel to be reintroduced into the tank and thus utilized as fuel for the aircraft. A further object of the invention is to provide an improved fueling system requiring less maintenance and reduce risk of accidents.

These objects are achieved by means of a fueling system for an aircraft, the system may comprise
  a tank comprising a compartment configured to be filled with fuel,
  a discharge conduit extending from the compartment to an outside of the tank, and a sampling arrangement comprising a sample container and a sample conduit extending from the compartment to the sample container.

The system further comprises a gas propellant arrangement comprising a pressurized gas source and a first gas connection between the pressurized gas source and the compartment, wherein, in a first mode of operation, the gas propellant arrangement is configured to provide pressurized gas through the first gas connection to the compartment, thereby driving fuel from the compartment of the tank through the discharge conduit and to an outside of the tank or driving fuel from the compartment of the tank through the sample conduit and into the sample container, wherein the gas propellant arrangement further comprises a second gas connection between the pressurized gas source and the sample container, wherein, in a second mode of operation, the gas propellant arrangement is configured to provide pressurized gas through the second gas connection to an inside of the sample container, thereby driving fuel from inside of the sample container through the sample conduit and back into the compartment of the tank.

By means of the first mode of operation of the gas propellant arrangement, when pressurized gas is brought through the first gas connection and into to the compartment, the fuel is driven from the compartment of the tank through the discharge conduit and to an outside of the tank. Thereby, the fuel is provided to the aircraft. Alternatively, by means of first mode of operation of the gas propellant arrangement, the fuel is driven from the compartment of the tank through the sample conduit and into the sample container. The configuration of the gas propellant arrangement enables fuel to be discharged and sampled without the use of pumps.

By means of the second mode of operation of the gas propellant arrangement, when pressurized gas is brought through the second gas connection and into to the sample container, the fuel is driven from the sample container through the sample conduit and back to the compartment of the container. The configuration of the gas propellant arrangement enables fuel that has been sampled to be reintroduced back into the compartment of the tank.

According to an embodiment of the invention, the sampling arrangement may further comprise a measuring unit configured to measure the humidity of the sampled fuel or a property dependent on the humidity of the sampled fuel. The measuring unit may be configured for measuring water in fuel. An example of a suitable water sensor is manufactured by Faudi Aviation GmbH in Germany and sold under trade name AFGUARD®. Further sensors known per se for measuring density, temperature pressure and level of fuel within the tank may also be used when desired or required.

According to an embodiment of the invention, the measuring unit may comprise a sensor unit arranged at the sample conduit, wherein the sensor unit is configured to sense the humidity or a property dependent on the humidity of the fuel passing through the sample conduit.

By means of measuring the humidity or a property dependent on the humidity at the sample conduit, the quality of the fuel in the compartment may be monitored over time. The second mode of operation of the gas propellant arrangement enables sampled fuel to be reintroduced. Accordingly, the invention enables the humidity or a property dependent on the humidity of the fuel to be monitored continuously and with improved utilisation of the fuel compared to prior art fueling systems.

According to an embodiment of the invention, the measuring unit may comprise a logic unit configured to receive information from the sensor unit and to determine a value of the humidity of the fuel passing through the sample conduit. The logic unit may be configured to determine a value on the humidity in the fuel based on the received information from the sensor unit.

According to an embodiment of the invention, the measuring unit may comprise a further sensor unit arranged at the discharge conduit, wherein the further sensor unit is configured to sense the humidity or a property dependent on the humidity of the fuel passing through the discharge conduit.

By means of measuring the humidity or a property dependent on the humidity at the discharge conduit a further confirmation is given that the fuel provided to the aircraft is of sufficient quality regarding the humidity content.

According to an embodiment of the invention, the logic unit may be configured to receive information from the further sensor unit and to determine a value of the humidity of the fuel passing through the discharge conduit. The logic unit is configured to determine a value on the humidity in the fuel through the discharge conduit based on the received information from the further sensor unit.

According to an embodiment of the invention, the measuring unit may comprises a control valve having an inlet in fluid communication with the discharge conduit and the sample conduit, and an outlet in fluid communication with the discharge conduit and the sample conduit, wherein the control valve between its inlet and outlet comprises a common conduit provided with the measuring unit configured to measure the humidity of the fuel or a property dependent on the humidity of the fuel flowing through the common conduit. This has the effect that a value of the humidity or a property dependent on the humidity of the fuel flowing through the discharge conduit and the sample conduit can be determined by means of a common measuring unit, such as a sensor. The control valve may be operated to direct fuel from one of the discharge conduit and the sample conduit through the common conduit provided with the measuring unit.

According to an embodiment of the invention measuring unit may be operatively connected to the sample conduit and the discharge conduit and configured to measure the humidity of fuel led through the measuring unit by means of an upstream valve arrangement configured for selectively opening for fluid communication from either the sample conduit or the discharge conduit, i.e. from one of the sample conduit and the discharge conduit at the time. The measuring unit is in this embodiment operatively connected to a downstream control valve configured to cooperate with the upstream valve arrangement so that fuel led into the measuring unit from the sample conduit upstream of the measuring unit is led into the sample conduit downstream of the measuring unit, and fuel led into the measuring unit from the discharge conduit upstream of the measuring unit is led into the discharge conduit downstream of the measuring unit. This has the effect that a value of the humidity or a property dependent on the humidity of the fuel flowing through the discharge conduit and the sample conduit can be determined by means of a common measuring unit, such as a sensor.

According to an embodiment of the invention the discharge conduit may comprise a measuring unit, the measuring unit comprises a further sensor unit configured to sense a humidity or a property dependent on the humidity of the fuel passing through the discharge conduit.

According to an embodiment of the invention the measuring unit may comprise a logic unit configured to receive information from the further sensor unit and to determine a value of the humidity of the fuel passing through the discharge conduit.

According to an embodiment of the invention, the compartment may comprise a sump portion configured to form a lowest part of the compartment, wherein the sample conduit is configured to extend into said sump portion. By means of sampling from the sump portion, a conservative measurement on the humidity content of the fuel in the compartment is provided.

According to an embodiment of the invention, the compartment may comprise a bottom portion located above the sump portion, wherein the discharge conduit is extending into said bottom portion. The discharge conduit receives fuel to be discharged from the bottom portion of the compartment that is configured to be located above the sump portion. Accordingly, the water content of the fuel discharged is likely to be lower than the sampled fuel from the sump portion of the compartment. Preferably, in an alternative embodiment the measurement is confirmed by the measurement by a further sensor unit at the discharge conduit.

According to an embodiment of the invention, the fueling system may comprise a control unit configured to set the gas propellant arrangement into the first or second mode of operation.

According to an embodiment of the invention, the gas propellant arrangement may comprise a first gas control valve at the first gas connection and a second gas control valve at the second gas connection, wherein the control unit is configured to control the first gas control valve and the second gas control valve so that in the first mode of operation, the first gas control valve is open and the second gas control valve is closed, and in the second mode of operation, the first gas control valve is closed and the second gas control valve is open. The control unit is configured to control the first gas control valve and the second gas control valve dependent on the desired mode of operation of the gas propellant arrangement.

According to an embodiment of the invention, the pressurized gas source may be a pressure vessel storing nitrogen. Nitrogen has the advantage of being an inert gas. Alternatively, the pressurized gas source provides $CO_2$ or dry gas through the first gas connection and the second gas connection.

Dry gas as blanketing gas on liquid surface at least limits moist air to condensate inside tank. This reduces water in fuel and the amount of separated water through fuel that may increase the amount of dissolved water in fuel. Thus, a dry gas as blanketing gas will reduce the frequency needed for draining of fuel from the tanks significantly. The result is less waste fuel, which is important with respect to an environmental point of view, and less exposure to operators which is important with respect to health of the operators.

According to an embodiment of the invention, the gas propellant arrangement may comprise a single pressurized gas source connected to the first gas connection and the second gas connection. The single pressurized gas source provides a simple and cost-effective configuration of the fueling system.

According to an embodiment of the invention, the gas propellant arrangement may comprise a first fuel control valve at the discharge conduit and a second fuel control valve at the sample conduit, wherein the first mode of operation of the gas propellant arrangement comprises a discharge mode of operation and a sampling mode of operation, wherein the control unit is configured to control the first fuel control valve and the second fuel control valve so that, in the discharge mode of operation, the first fuel control valve is open and the second fuel control valve is closed, and in the sampling mode of operation, the first fuel control valve is closed and the second fuel control valve is open.

The first mode of operation may comprise two modes, the discharge mode of operation and the sampling mode of operation. In the discharge mode of operation, fuel is discharged through the discharge conduit by means of that the first gas control valve is open, the second gas control valve is closed, the first fuel control valve is open and the second fuel control valve is closed. In sampling mode of operation, the fuel is sampled through the sample conduit into the sample container by means of that the first gas control valve is open, the second gas control valve is closed, the first fuel control valve is closed and the second fuel control valve is open.

According to an embodiment of the invention, the measuring unit may be configured to measure the humidity of the sampled fuel or a property dependent on the humidity of the sampled fuel during the sampling mode of operation of the gas propellant arrangement.

According to an embodiment of the invention, the measuring unit may be configured to measure the humidity or a property dependent on the humidity of the fuel through the discharge conduit during the discharge mode of operation of the gas propellant arrangement.

According to an embodiment of the invention, the fueling system may further comprise a fuel density-controlled valve between the sump portion and the bottom portion of the compartment.

According to an embodiment of the invention, the fuel density-controlled valve may comprise a closing element having a density between that of water and that of fuel so that the closing element floats in water and to sink in fuel. The fuel density-controlled valve may thus be configured to enable water containing fuel to pass through the valve while preventing fuel lacking water to pass through the valve.

According to an embodiment of the invention, the sample container may comprise a drainage outlet configured to be arranged in a lowest portion of the sample container, wherein the fueling system may comprise a further fuel density-controlled valve between the drainage outlet and the sample conduit.

According to an embodiment of the invention, the further fuel density-controlled valve may comprise a closing element having a density between that of water and that of fuel so that the closing element floats in water and to sink in fuel. The further fuel density-controlled valve may thus be configured to enable water containing fuel to pass through the valve while preventing fuel lacking water to pass through the valve.

According to an embodiment of the invention, the tank may comprise an opening between the compartment and an outside of the tank, wherein fueling system may comprise a pressure release valve at the opening. The pressure release valve may be an emergency pressure/vacuum relief valve.

The objects of the invention are further obtained by means of a method for operating the fueling system according to any of above embodiments. The method comprises the step of setting the gas propellant arrangement to the first mode of operation by means of providing pressurized gas through the first gas connection to the compartment, thereby driving fuel from the compartment of the tank through the discharge conduit, and setting the gas propellant arrangement to the second mode of operation by means of providing pressurized gas through the second gas connection to an inside of the sample container, thereby driving fuel from inside of the sample container through the sample conduit and back into the compartment of the tank.

According to an embodiment of the invention, the method may comprise the step of setting the gas propellant arrangement to the discharge mode of operation, by setting the first fuel control valve to an open state and the second fuel control valve to a closed state.

According to an embodiment of the invention, the method may comprise the step of setting the gas propellant arrangement to the sampling mode of operation, by setting the first fuel control valve to a close state and the second fuel control valve to an open state.

According to an embodiment of the invention, the method may comprise the step of measuring the humidity or a property dependent on the humidity of the fuel passing through the sample conduit.

According to an embodiment of the invention, the method may comprise the step of measuring the humidity or a property dependent on the humidity of the fuel passing through the discharge conduit.

The objects of the invention are further obtained by means of use of a fueling system according to any of above embodiments.

BRIEF DESCRIPTION OF DRAWINGS

In the following is described examples of preferred embodiments illustrated in the accompanying drawings, wherein.

DETAIL DESCRIPTION OF THE INVENTION

Figure 1A:
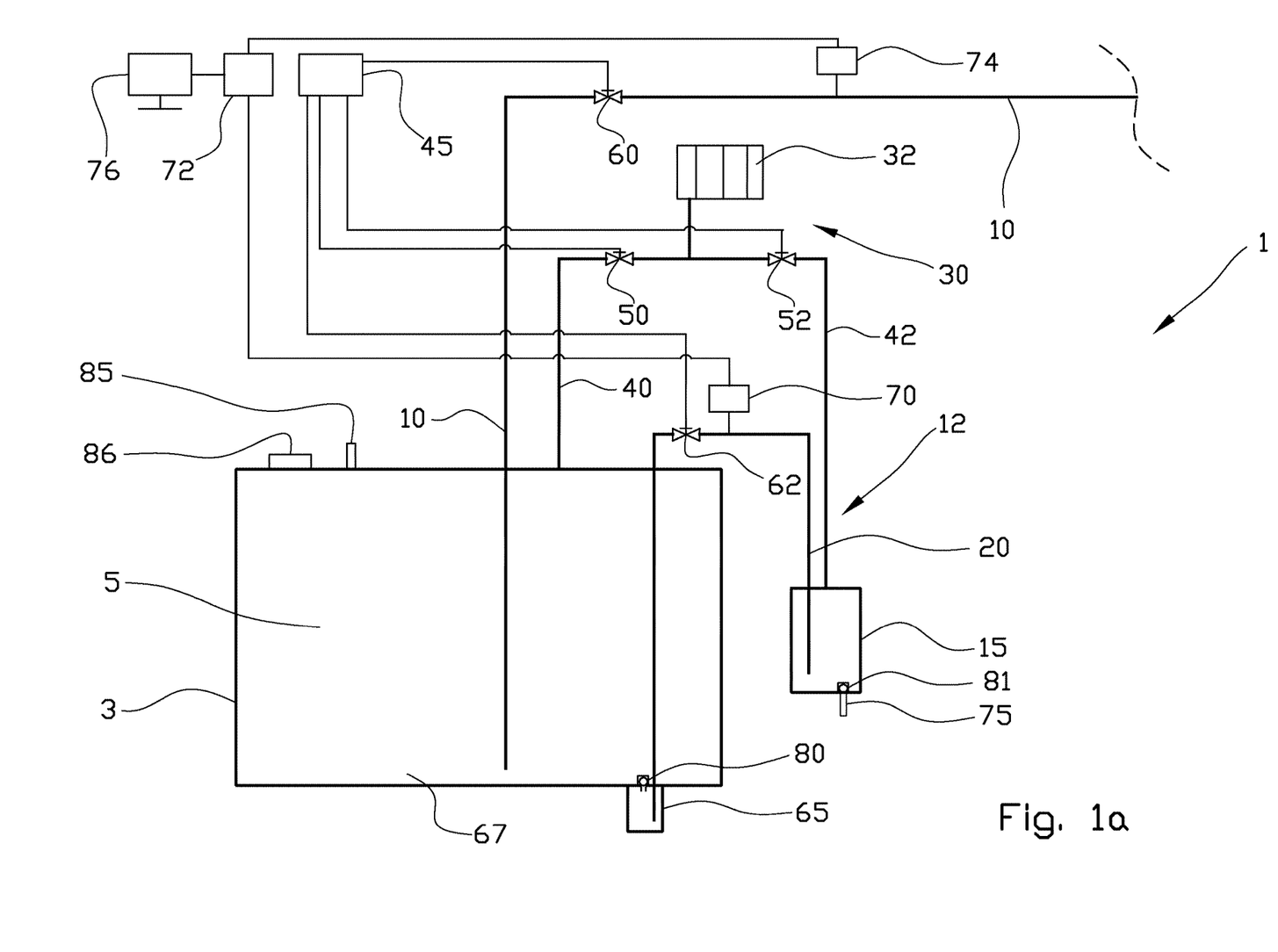
FIG. 1a discloses a fueling system according to an embodiment of the invention.

In FIG. 1a is a fueling system 1 according to an embodiment of the invention disclosed. The fueling system 1 comprises a tank 3 comprising a compartment 5 configured to be filled with fuel, in particular fuel for an aircraft. The fueling system 1 further comprises a discharge conduit 10 and a sampling arrangement 12. The discharge conduit 10 extends from the compartment 5, through an opening in the tank 3 and to an outside of the tank 3. The sampling arrangement 12 comprises a sample container 15 and a sample conduit 20 extending from the compartment 5 to the sample container 15. It should be noted that in an alternative embodiment (not shown) the tank 3 may comprise more than the single tank shown in for example FIG. 1a. In such an alternative embodiment two or more tanks may be connected to a common discharge conduit 10, wherein fluid communication from each tank is controlled by means of valves known per se.

The fueling system 1 further comprises a gas propellant arrangement 30 comprising a pressurized gas source 32 and a first gas connection 40 and a second gas connection 42. The first gas connection 40 is arranged extending between the pressurized gas source 32 and the compartment 5. The second gas connection 42 is arranged extending between the pressurized gas source 32 and the sample container 15. The first gas connection 40 is configured to provide gas to the compartment 5 so that the compartment 5 is pressurized in respect to the outside of the tank 3. The second gas connection 42 is configured to provide gas to the sample container 15 so that the sample container 15 is pressurized in respect to the compartment 5.

The pressurized gas source 32 is for example a pressure vessel storing nitrogen. Alternatively, the pressurized gas source 32 provides $CO_2$ or dry gas through the first gas connection 40 and the second gas connection 42. In the disclosed embodiment, the gas propellant arrangement 30 comprises a so-called nitrogen bank connected to the first gas connection 40 and the second gas connection 42.

The gas propellant arrangement 30 comprises a first mode of operation and a second mode of operation.

In the first mode of operation, the gas propellant arrangement 30 is configured to provide pressurized gas through the first gas connection 40 to the compartment 5, thereby driving fuel from the compartment 5 of the tank 3 through the discharge conduit 10 and to an outside of the tank 3 or driving fuel from the compartment 5 of the tank 3 through the sample conduit 20 and into the sample container 15.

In the second mode of operation, the gas propellant arrangement 30 is configured to provide pressurized gas through the second gas connection 42 to an inside of the sample container 15, thereby driving fuel from inside of the sample container 15 through the sample conduit 20 and back into the compartment 5 of the tank 3.

The fueling system 1 further comprises a control unit 45 configured to set the gas propellant arrangement 30 into the first or second mode of operation.

The gas propellant arrangement 30 further comprises a first gas control valve 50 at the first gas connection 40 and a second gas control valve 52 at the second gas control connection 42. The first gas control valve 50 and the second gas control valve 52 each have an open and a close state.

In the first mode of operation, the control unit 45 is configured to set the first gas control valve 50 to an open state and the second gas control valve 52 to a close state. Thereby, the gas propellant arrangement 30 is providing pressurized gas through the first gas connection 40 and into the compartment 5.

Correspondingly, in the second mode of operation, the control unit 45 is configured to set the first gas control valve 50 to a closed state and the second gas control valve 52 to and open state. Thereby, the gas propellant arrangement 30 is providing pressurized gas through the second gas connection 42 and into the sample container 15.

Moreover, the first mode of operation of the gas propellant arrangement 30 comprises two sub-modes, a discharge mode of operation and a sampling mode of operation. In the discharge mode of operation, fuel is discharged through the discharge conduit 10 to an outside of the tank 3. In the sampling mode of operation, fuel is sampled through the sample conduit 20 into the sample container 15.

The gas propellant arrangement 30 further comprises a first fuel control valve 60 at the discharge conduit 10 and a second fuel control valve 62 at the sample conduit 20. The first fuel control valve 60 and the second fuel control valve 62 each have an open and a close state.

In the discharge mode of operation, the control unit 45 is configured to set the first gas control valve 50 to the open state, the second gas control valve 52 to the closed state, the first fuel control valve 60 to the open state and the second fuel control valve 62 to the close state. Thereby, fuel from the compartment 5 is driven through the discharge conduit 10 while fuel is prevented from passing through the sample conduit 20.

Correspondingly, in the sampling mode of operation, the control unit 45 is configured to set the first gas control valve 50 to the open state, the second gas control valve 52 to the closed state, the first fuel control valve 60 to the closed state and the second fuel control valve 62 to the open state. Thereby, fuel is prevented from passing through the discharge conduit 10 while fuel is driven through the sample conduit 20 and into the sample container 15.

In the disclosed embodiment, the compartment 5 of the tank 3 comprises a sump portion 65 and a bottom portion 67. The sump portion 65 is configured to form a lowest part of the compartment 5. Thereby, possible water containing fuel in the compartment 5 will sink into the sump portion 65. The bottom portion 67 is located above the sump portion 65 and is therefore likely to have fuel containing less water than the sump portion 65. The discharge conduit 10 is extending into the bottom portion 67 and accordingly the discharge conduit 10 discharges fuel from the bottom portion 67 of the compartment 5. The sample conduit is extending into sump portion 65 and accordingly samples fuel from the sump portion 65 of the compartment 5. By such an arrangement, and end portion of the discharge conduit 10 may be closer to the bottom portion 67 than the minimum 150 mm stated in CAP 437.

In the disclosed embodiment, the sampling arrangement 12 further comprises measuring unit configured to measure the humidity of the sampled fuel or a property dependent on the humidity of the sampled fuel. The measuring unit comprise a sensor unit 70 arranged at the sample conduit 20 and a logic unit 72. The sensor unit 70 is configured to sense the humidity or a property dependent on the humidity of the fuel passing through the sample conduit 20. The logic unit 72 is configured to receive information from the sensor unit 70 and to determine a value of the humidity and other parameters as applicable of the fuel passing through the sample conduit 20 based on the received information.

In the disclosed embodiment, the measuring unit comprises a further sensor unit 74 arranged at the discharge conduit 10. The further sensor unit 74 is configured to sense the humidity or a property dependent on the humidity of the fuel passing through the discharge conduit 10. Correspondingly, the logic unit 72 is configured to receive information from the further sensor unit 74 and to determine a value of the humidity of the fuel passing through the discharge conduit 10. In the disclosed embodiment, the measuring unit further comprises a display unit 76 for displaying the determined value of the humidity of the fuel passing through the sample conduit 20 and discharge conduit 10 based on the received information.

In the disclosed embodiment, the fueling system 1 further comprises a fuel density-controlled valve 80 between the sump portion 65 and the bottom portion 67 of the compartment 5. The fuel density-controlled valve 80 is configured with weight and buoyancy that enables it to float in the water and to sink in fuel, i.e. the fuel density-controlled valve 80 typically comprises a closing element having a density between that of water and that of fuel, such as for example 0.9. The fuel density-controlled valve 80 is configured to allow water possibly with limited amounts of fuel to pass into the sump portion 65 while preventing fuel substantially without water from passing into the sump portion 65.

In the disclosed embodiment, the sample container 15 comprises a drainage outlet 75 configured to be arranged in a lowest portion of the sample container 15. The fueling system 1 further comprises a further fuel density-controlled valve 81 between the drainage outlet 75 and the sample conduit 20. Correspondingly, the further fuel density-controlled valve 81 is configured to allow water with possible limited amounts of fuel to pass to the drainage outlet 75 while preventing fuel substantially without water from passing to the drainage outlet 75.

In the disclosed embodiment, the sample container 15 is arranged outside the tank 3. However, the sample container 15 may in an alternative embodiment be arranged within the tank 3. The drainage outlet 75 will in such an alternative embodiment extend through a portion of the tank 3, typically through a wall portion.

Figure 1B:
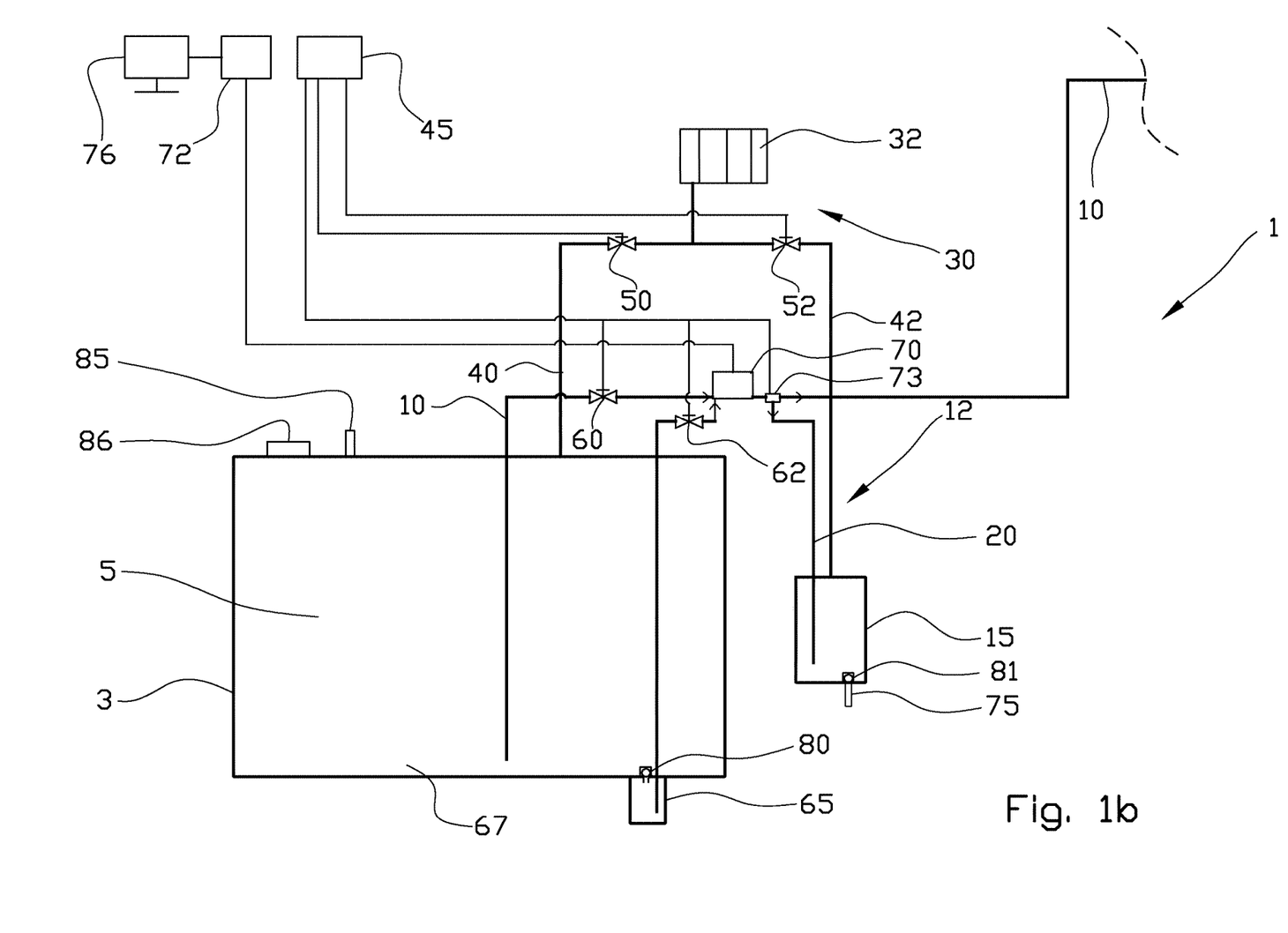
FIG. 1b discloses a fueling system according to an embodiment of the invention.

In the embodiment shown in FIGS. 1a and 1b, the tank 3 is penetrated by conduits 10, 20, 40 only in its top portion. A risk of leaking fuel is therefore substantially eliminated.

In the disclosed embodiments, the tank 3 is arranged without a drainage for discharging water containing fuel from the sump portion 65 of the compartment 5. Instead, the drainage of water containing fuel is done by means of the drainage outlet 75 located at the sample container 15.

In the disclosed embodiments, the tank 3 comprises an opening between the compartment 5 and an outside of the tank 3. The opening is provided with an emergency pressure/vacuum relief valve 85 for assuring that the pressure in the tank 3 is not higher/lower than a predetermined value. The valve is configured for being activated if a pressure within the tank is higher, for example 3-5 barg than a pressure from the pressurized gas source 32. To prevent implosion, the valve 85 is configured being activated if pressure is lower than a vacuum setpoint of typically −0.2 barg.

The tank 3 is further provided with a manhole 86 known per se and/or a connection for filling the tank with fuel.

The embodiment disclosed in FIG. 1b has many similarities with the embodiment disclosed in FIG. 1a. The main difference is that in FIG. 1b there is only one measuring unit 70. Fuel flow into the measuring unit 70 is controlled by means of the first fuel control valve 60 and the second fuel control valve 62. Thus, the measuring unit 70 has an inlet in fluid communication with the discharge conduit 10 and the sample conduit 20, and an outlet in selective fluid communication with the discharge conduit 10 and the sample conduit 12 by means of a control valve 73. Within the measuring unit 70 the fuel flows via a common conduit provided with a sensor for sensing the humidity of the fuel or a property dependent on the humidity of the fuel flowing therethrough. This has the effect that a value of the humidity, or a property dependent on the humidity, of the fuel flowing through the discharge conduit 10 and the sample conduit 20 can be determined by means of only one common measuring unit 70, such as a sensor. At a downstream side of measuring unit 70, the control valve 73 is operable to direct fuel into one of the discharge conduit 10 and the sample conduit 20.

In an alternative embodiment (not shown) to the embodiment shown in FIG. 1b, the measuring unit comprises a control valve having an inlet in fluid communication with the discharge conduit 10 and the sample conduit 20, and an outlet in fluid communication with the discharge conduit 10 and the sample conduit 20, wherein the control valve between its inlet and outlet comprises a common conduit provided with the measuring unit configured to measure the humidity of the fuel or a property dependent on the humidity of the fuel flowing through the common conduit.

Figure 2:
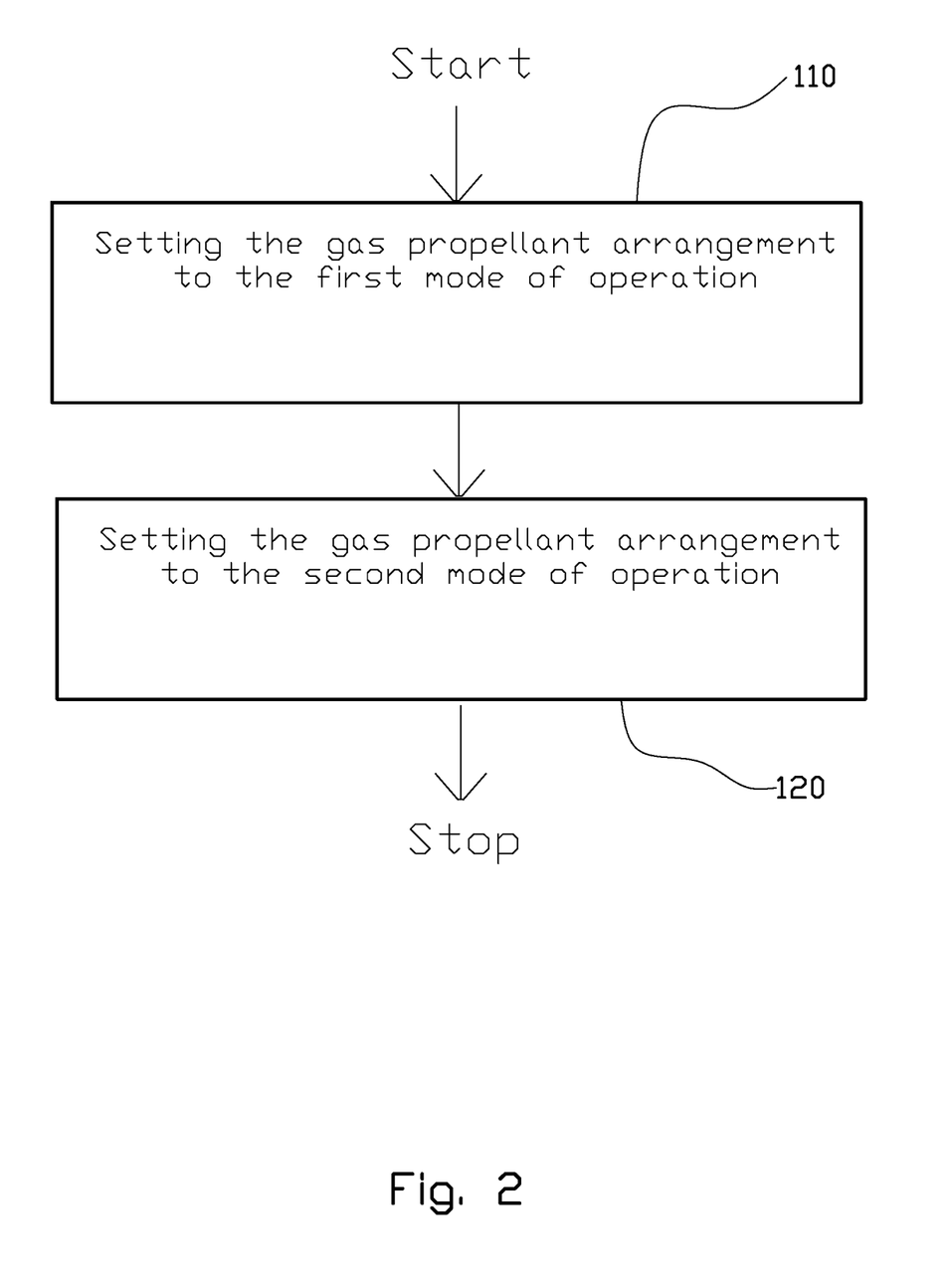
FIG. 2 discloses a flow chart of a method for controlling a fueling system according to a first embodiment of the invention.

In FIG. 2 is a flow chart of a method for controlling a fueling system 1 according to a first embodiment of the invention disclosed.

In a step 110, the method comprises setting the gas propellant arrangement 30 to the first mode of operation by means of providing pressurized gas through the first gas connection 40 to the compartment 5, thereby driving fuel from the compartment 5 of the tank 3 through the discharge conduit 10 and to an outside.

In a step 120, the method comprises setting the gas propellant arrangement 30 to the second mode of operation by means of providing pressurized gas through the second gas connection 42 to an inside of the sample container 15, thereby driving fuel from inside of the sample container 15 through the sample conduit 20 and back into the compartment 5 of the tank 3.

Figure 3:
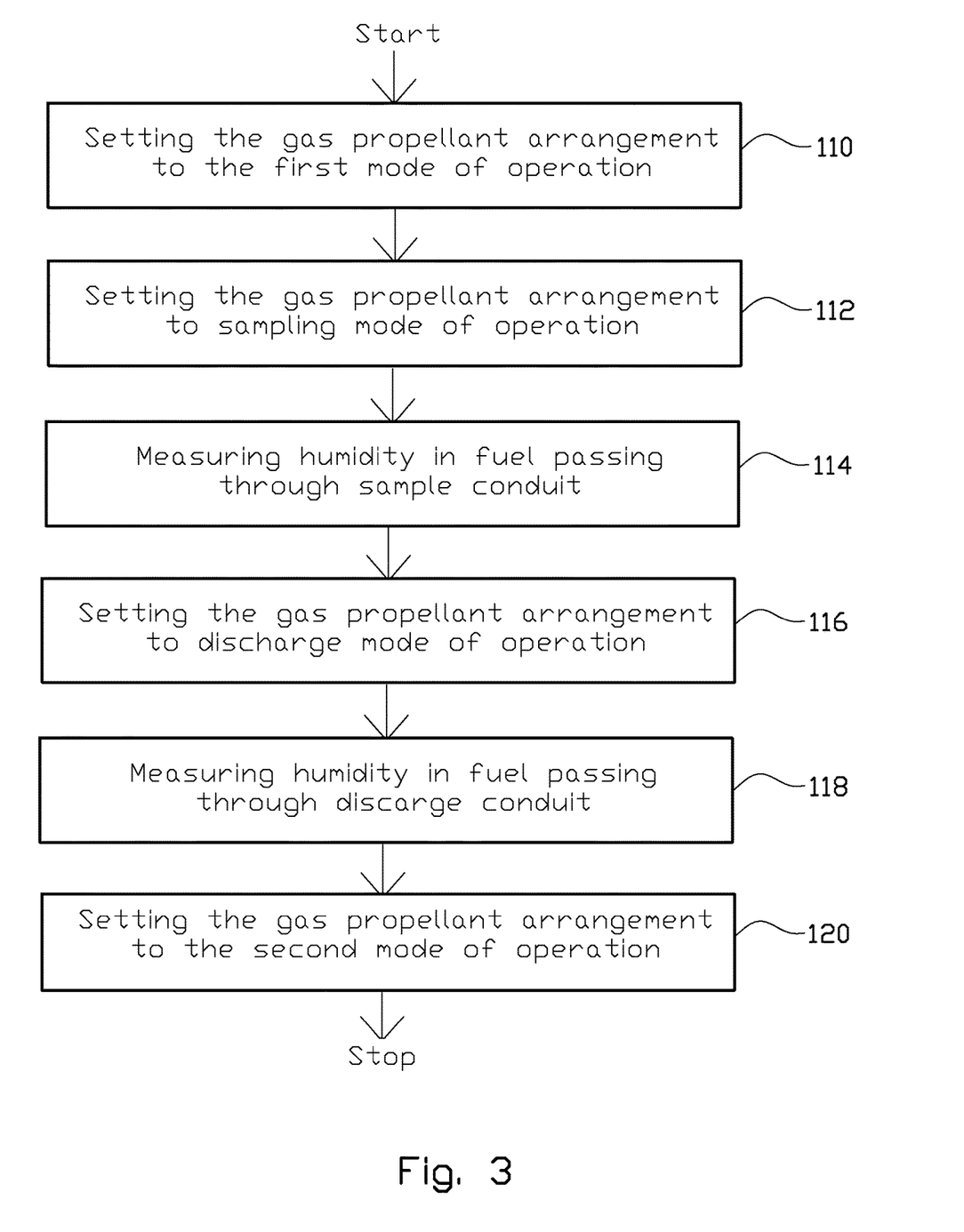
FIG. 3 discloses a flow chart of a method for controlling a fueling system according to a second embodiment of the invention.

In FIG. 3 is a flow chart of a method for controlling a fueling system 1 according to a second embodiment of the invention disclosed. The method differs from the embodiment in FIG. 2 with the following steps:

In a step 112, the method comprises setting the gas propellant arrangement 30 to the sampling mode of operation, by setting the first fuel control valve 60 to a close state and the second fuel control valve 62 to an open state.

In a step 114, the method comprises measuring the humidity or a property dependent on the humidity of the fuel passing through the sample conduit 20.

In a step 116, the method comprises setting the gas propellant arrangement 30 to the discharge mode of operation, by setting the first fuel control valve 60 to an open state and the second fuel control valve 62 to a closed state.

In a step 118, the method comprises measuring the humidity or a property dependent on the humidity of the fuel passing through the discharge conduit 10.

It should be noted that the above-mentioned embodiments illustrate rather than limit the invention, and that those skilled in the art will be able to design many alternative embodiments without departing from the scope of the appended claims. Use of the verb "comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A fueling system for an aircraft, wherein the fueling system comprises:
   a tank comprising a compartment configured to be filled with fuel,
   a discharge conduit extending from the compartment to an outside of the tank,
   a sampling arrangement comprising a sample container and a sample conduit extending from the compartment to the sample container,
   wherein the fueling system further comprises a gas propellant arrangement comprising a pressurized gas source and a first gas connection between the pressurized gas source and the compartment,
   wherein, in a first mode of operation, the gas propellant arrangement is configured to provide pressurized gas through the first gas connection to the compartment, thereby driving fuel from the compartment of the tank through the discharge conduit and to an outside of the tank or driving fuel from the compartment of the tank through the sample conduit and into the sample container,
   wherein the gas propellant arrangement further comprises a second gas connection between the pressurized gas source and the sample container, and
   wherein, in a second mode of operation, the gas propellant arrangement is configured to provide pressurized gas through the second gas connection to an inside of the sample container, thereby driving fuel from inside of the sample container through the sample conduit and back into the compartment of the tank.

2. The fueling system according to claim 1, wherein the sampling arrangement further comprises a measuring unit configured to measure the humidity of the sampled fuel or a property dependent on the humidity of the sampled fuel.

3. The fueling system according to claim 2, wherein the measuring unit comprises a logic unit configured to receive information from a sensor unit and to determine a value of the humidity of the fuel passing through the sample conduit.

4. The fueling system according to claim 2, wherein the measuring unit comprises a further sensor unit arranged at the discharge conduit, wherein the further sensor unit is configured to sense the humidity or a property dependent on the humidity of the fuel passing through the discharge conduit.

5. The fueling system according to claim 4, wherein the logic unit is configured to receive information from the further sensor unit and to determine a value of the humidity of the fuel passing through the discharge conduit.

6. The fueling system according to claim 2, wherein the measuring unit is operatively connected to the sample conduit and the discharge conduit and configured to measure the humidity of fuel led through the measuring unit by an upstream valve arrangement configured for selectively opening for fluid communication from either the sample conduit or the discharge conduit, wherein the measuring unit is operatively connected to a downstream control valve configured to cooperate with the upstream valve arrangement so that fuel led into the measuring unit from the sample conduit upstream of the measuring unit is led into the sample conduit downstream of the measuring unit, and fuel led into the measuring unit from the discharge conduit upstream of the measuring unit is led into the discharge conduit downstream of the measuring unit.

7. The fueling system according to claim 2, wherein the measuring unit is configured to measure the humidity of the sampled fuel or a property dependent on the humidity of the sampled fuel during a sampling mode of operation of the gas propellant arrangement.

8. The fueling system according to claim 2, wherein the measuring unit is configured to measure the humidity or a property dependent on the humidity of the fuel through the discharge conduit during a discharge mode of operation of the gas propellant arrangement.

9. The fueling system according to claim 1, wherein the sampling arrangement further comprises a measuring unit that comprises a sensor unit arranged at the sample conduit, wherein the sensor unit is configured to sense the humidity or a property dependent on the humidity of the fuel passing through the sample conduit.

10. The fueling system according to claim 1, wherein the discharge conduit comprises a measuring unit, the measuring unit comprises a further sensor unit configured to sense a humidity or a property dependent on the humidity of the fuel passing through the discharge conduit.

11. The fueling system according to claim 10, wherein the measuring unit comprises a logic unit configured to receive information from the further sensor unit and to determine a value of the humidity of the fuel passing through the discharge conduit.

12. The fueling system according to claim 1, wherein the compartment comprises a sump portion configured to form a lowest part of the compartment, wherein the sample conduit is configured to extend into said sump portion.

13. The fueling system according to claim 1, wherein the compartment comprises a bottom portion located above a sump portion, wherein the discharge conduit is extending into said bottom portion.

14. The fueling system according to claim 1, wherein the fueling system comprises a control unit configured to set the gas propellant arrangement into the first or second mode of operation.

15. The fueling system according to claim 14, wherein the gas propellant arrangement comprises a first gas control valve at the first gas connection and a second gas control valve at the second gas connection, wherein the control unit is configured to control the first gas control valve and the second gas control valve so that in the first mode of operation, the first gas control valve is open and the second gas control valve is closed, and in the second mode of operation, the first gas control valve is closed and the second gas control valve is open.

16. The fueling system according to claim 14, wherein the gas propellant arrangement comprises a first fuel control valve at the discharge conduit and a second fuel control valve at the sample conduit, wherein the first mode of operation of the gas propellant arrangement comprises a discharge mode of operation and a sampling mode of operation, wherein the control unit is configured to control the first fuel control valve and the second fuel control valve so that, in the discharge mode of operation, the first fuel control valve is open and the second fuel control valve is closed, and in the sampling mode of operation, the first fuel control valve is closed and the second fuel control valve is open.

17. The fueling system according to claim 1, wherein the fueling system further comprises a fuel density-controlled valve between a sump portion and a bottom portion of the compartment.

18. The fueling system according to claim 1, wherein the sample container comprises a drainage outlet configured to be arranged in a lowest portion of the sample container, wherein the fueling system comprises a further fuel density-controlled valve between the drainage outlet and the sample conduit.

19. A method for controlling a fueling system according to claim 1, wherein the method comprises the step of:
   setting the gas propellant arrangement to the first mode of operation by means of providing pressurized gas through the first gas connection to the compartment, thereby driving fuel from the compartment of the tank through the discharge conduit, and
   setting the gas propellant arrangement to the second mode of operation by providing pressurized gas through the second gas connection to an inside of the sample container, thereby driving fuel from inside of the sample container through the sample conduit and back into the compartment of the tank.

20. The method according to claim 19, wherein the method comprises the step of:
   setting the gas propellant arrangement to a discharge mode of operation, by setting a first fuel control valve to an open state and a second fuel control valve to a closed state.

21. The method according to claim 19, wherein the method comprises the step of:
   setting the gas propellant arrangement to a sampling mode of operation, by setting a first fuel control valve to a close state and a second fuel control valve to an open state.

22. The method according to claim 19, wherein the method comprises the step of:
   measuring the humidity or a property dependent on the humidity of the fuel passing through the sample conduit.

23. The method according to claim 19, wherein the method comprises the step of:
   measuring the humidity or a property dependent on the humidity of the fuel passing through the discharge conduit.

* * * * *